June 4, 1968 S. CALVINO Plant Pat. 2,814
HYBRID TEA ROSE PLANT
Filed Nov. 10, 1966
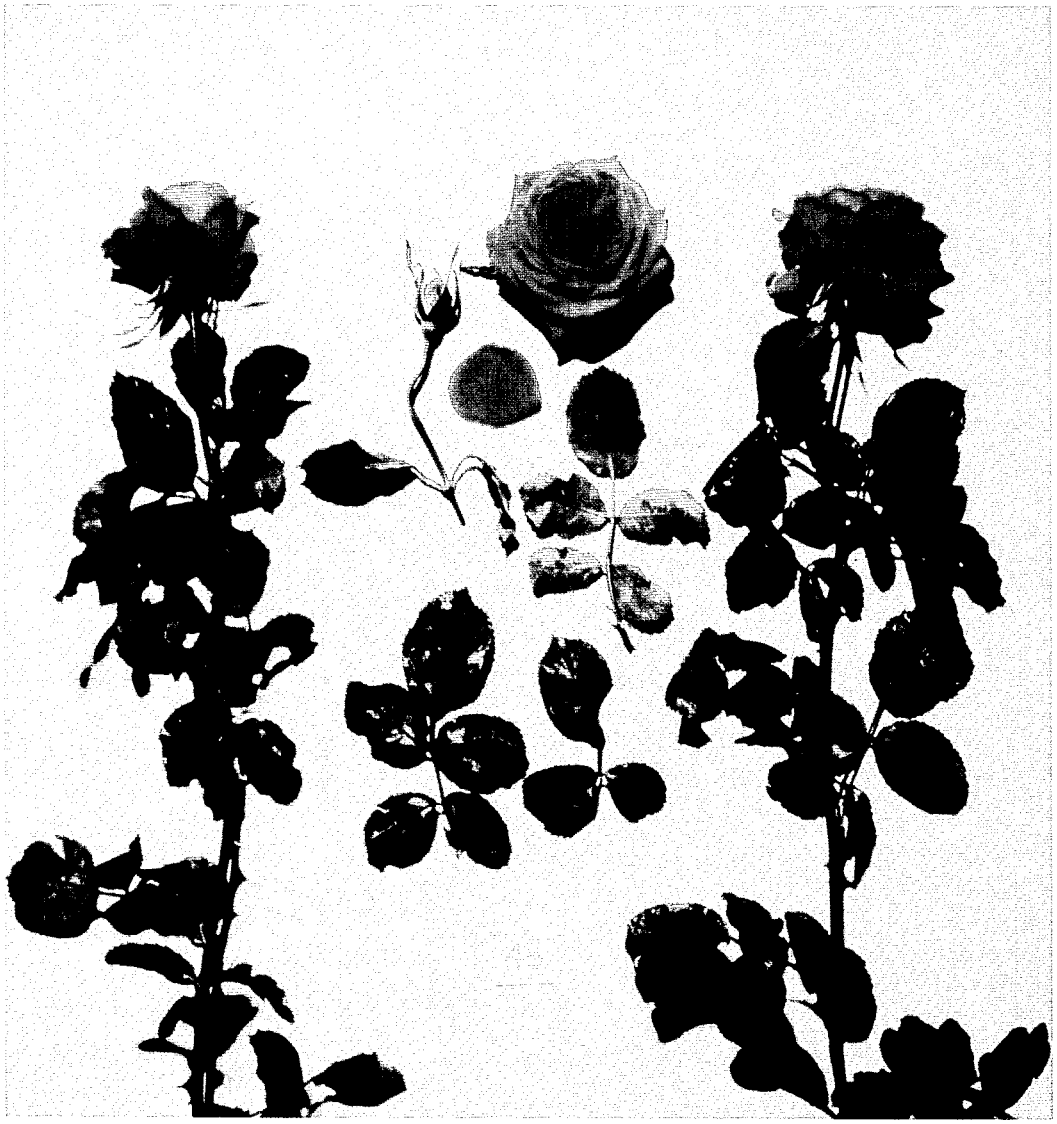

United States Patent Office

Plant Pat. 2,814
Patented June 4, 1968

2,814
HYBRID TEA ROSE PLANT

Stefano Calvino, Strada Coldirodi,
65 San Remo, Italy

Filed Nov. 10, 1966, Ser. No. 593,592
Claims priority, application Italy, Nov. 11, 1965, 25,011/65
1 Claim. (Cl. Plt.—20)

The new variety of rose which is the subject of the present invention has been developed by the applicant for the purpose of making available to large-scale rose growers for cut flower production a new variety capable of interesting consumers by virtue of a harmonious combination of forms and colours of the flower and of the stems, and possessing superior features from the viewpoint of vigour and growth, output of stems for cutting, resistance to disease, etc. such as to render it more suitable for large-scale cultivation than varieties previously grown.

The flower colour range that has been chosen is vivid red, in a particular shade which is in great demand on international consumer markets.

For the above-stated purpose the applicant has carried out extensive research, his working method being the genetic cross-breeding of different varieties, appropriately chosen so as to bring together in the same plant, according to the laws of the hereditary transmission of the characteristics in plants grown from seed, those features proposed as the object of the research.

The plant which is the subject of the present invention, which is different from the others already known, has been obtained by means of the artificial fecundation of flowers of a hybrid tea rose variety with pollen from a polyantha rose with red flowers known in commerce by the name of "Ninfa." It has been isolated and selected from a wide stock of hybrid varieties, produced by the aforementioned cross-breeding, as satisfying, in the greatest possible measure, the selected requisites.

The plant which is the subject of the present invention can easily be reproduced in any number of specimens, all having the features of the original plant, by means of one of the vegetation development methods of the plants (grafting, cutting, layering). Such methods of reproduction may be continued indefinitely, even when starting from plants derived from the original by one of the vegetation development methods, and by means of the method the variety which is the subject of the present invention indefinitely conserves all its distinctive features in the subsequent descendants constantly and faithfully. It may be used, therefore, for large-scale cultivation where it has already proved to be of notable value for the production of cut market flowers.

The description which follows is a list, provided as a non-limiting example of the features which, taken altogether, define the variety according to the present invention and permit its identification.

This description has been based on a set of plants grafted about two years ago on *Rosa indica major* and cultivated according to industrial criteria in the open air and in full soil on a sunny hillside, at San Remo in the month of September.

Reference should always be made to these climatic and seasonal conditions with regard to the plant and the present description. Any differences which, as a result of different conditions of climate, season, soil or method of cultivation, may be encountered between certain features of the plant and the corresponding ones of the description must be considered normal and do not modify the essence of the present invention, at least so long as it is possible to identify the variety by means of the collection of features given in the description by repeating the cultivation under the same conditions as those of the plants described.

In the description the colours have been named according to the tables of the Horticultural Colour Chart by Robert F. Wilson (indicated in the text by the initials HCC) except in those cases in which the colours were absent from the tables or where its indication is sufficiently clear according to common parlance.

Classification: Botanical and commercial—hybrid tea× polyantha.

Stock: Unknown hybride of HT×"Ninfa," polyantha with red flowers.

*Plant*

Growth: Very vigorous plant, large, bushy. Compact, erect growth. Leaves of average size, abundant, up the entire height of the plant.

Average height: For plants of two years' grafting on *Rosa indica major*—140–170 cm. from the ground.

Roots: Shapes and sizes varying according to the kind of graft recipient used. On *Rosa indica major* the roots are vigorous and sturdy in number 2–4 main roots, woody, up to 50–60 cm. long and with 8–12 mm. collar diameter, together with others more slender and ramified. Root hairs long and of average thickness. Colour blackish-brown.

Collar and stem: Varying with the kind of graft recipient. In plants on *Rosa indica major* the stem consists of the graft bearing cutting, 20–30 cm. long on an average and with an average diameter of 15–20 mm. at the base, cylindrical or slightly conical towards the top.

Main branches: Numerous, starting raywise or at short intervals from the grafting point. On an average 6–8 divergent at the base, afterwards ascending and vertical.

Tendency of the plant to vegetate from the base.

*Shape.*—Cylindrical or slightly conical towards the top, articulated in numerous internodes 40–70 mm. long on an average. Nodes not very marked, each bearing one leaf.

*Size.*—Extremely variable according to the method of pruning. Average length from 40–60 cm. up to 100–115 cm. for the unpruned shoots of the year which reach directly to the flower. Average diameter at the base 10–15 mm.

*Bark.*—Smooth hairless, pruninose, opaque.

*Colour.*—Close to Spinach Green (HCC page 187, shades 60–60/1/2/3) tinted lengthwise with Pomegranate Red (HCC page 192, shades 18/1/2/3).

*Consistency.*—Firm and woody.

*Prickles.*—Large—fairly numerous or numerous, varying sizes, occurring irregularly on the branches, detachable with average facility from the bark. Shape—triangular with concave sides. Point sharp and straight. Perpendicular to the branch or with slight downward inclination. Oval elongated base, narrower in the lower part. Size—average length, 3–10 mm.; breadth 3–15.; thickness, 2–4 mm. Colour—close to Oxblood Red (HCC page 191, shades 23/1/2/3) tinted with green at the point. Acicular prickles—not numerous, more frequent at the base of the main branches, average length, 3–4 mm.; breadth, 4–5 mm. at the base and 1–2 mm. thick.

Flower stems: Numerous, 3–5 on an average for each main branch, erect, only slightly divergent, graceful.

*Shape.*—Cylindrical-conical towards the top, articulated in numerous internodes on an average 60–70 mm. long. Nodes slightly marked or average.

*Size.*—Average length 60–100 cm. Average diameter at the base 5–8 mm., at half stem 4–6 mm., under the flower 2–4 mm.

*Bark.*—Smooth, hairless, of medium thickness, satiny or pruinose.

*Consistency.*—Firm and woody.

*Prickles.*—Average size, not numerous or average, occurring on the stems in the number of 2–5 per internode, fairly easily detachable, thicker at the base of the stems. Shape—triangular, lower side more concave and point sharp, straight, inclined downwards. Base oval, very elongated. Size—average length, 7–10 mm.; average breadth, 8–14 mm.; thickness, 2–3 mm. Colour—Oxblood Red (HCC page 191, shade 23/3).

Leaves: Average size, borne singly on each node, with midrib slightly swollen at the point of insertion, furled round approx. half the circumference of the stem.

*Shape.*—Composed of 3–5–7 folioles, generally 7 at the base, 5 in the middle and 3 in the top leaves. Folioles inserted in opposite pairs plus a terminal foliole on a sturdy midrib, angled at the nodes, with marked longitudinal groove on the right side with hairy and glandulous edges, 3–4 small prickles not always present on the underleaf.

*Size.*—Average length of the leaf, 90–160 mm.; average breadth, 70–130 mm.

*Folioles.*—Shape—slightly varying according to the position on the midrib. Limb oval, spear-shaped in the base folioles, rather more rounded with sharp point in the terminal foliole. Limb generally concave on the centre nervation wavy or flat, slightly bubbly between the nervations. Blades serrated with small or average teeth sharp and pointing towards the tip of the foliole. Peduncle of the foliole short.

*Size.*—Variable with the position on the stem and on the midrib. For 7-foliole leaves starting from the base: 1st pair—length, 20–25 mm.; breadth, 10–15 mm. 2nd pair—length, 30–35 mm.; breadth, 18–25 mm. 3rd pair—length, 35–40 mm.; breadth, 20–30 mm. Terminal foliole—length, 45–60 mm.; breadth, 30–40 mm.

*Colour.*—Right side—between Parsley Green (HCC page 193, shades 62–62/1) and Spinach Green (HCC page 187, shades 60–60/1). Underside—between Lavender Green (HCC page 196, shades 61–61/1) and Willow Green (HCC page 199, shades 62–62/1) sometimes tinted with reddish-brown at the base of the foliole.

*Flower*

Main flower terminal on the stem on a slender flower peduncle, of average firmness, average length 80–120 and average diameter 2–5 mm., smooth or with few glandular hairs. Secondary buds 2–3 in number around the main flower, with tendency to flower at the same time as the latter, borne by secondary stems, slender, and of various height, inserted in pairs at the base of the flower peduncle or on the higher nodes of the stem, accompanied by rudimentary leaves.

Closed flower bud: Rounded, globose, with tip of average sharpness, terminating in short foliaceous appendices. Slender, filiform, spear-shaped appendices, divergent from the bud.

*Size.*—Length 30–35 mm., including the foliaceous appendices. Diameter 14–20 mm.

Calyx: Thalamus—hemispherical urn shape, slightly elongated, length 10–12 mm. and diameter 8–10 mm.

*Sepals.*—5 in number, drooping in average manner on the thalamus when the corolla is open, deciduous when fruit is mature.

*Shape.*—Trianuglar, spear-shaped limb, with sharp tip almost always terminated in slender foliaceous spear-shaped appendices, length up to 15–25 mm. Sepals flat at the base with raised edges near the tip. Sepal edges hairy, bearing on each side 1–2 slender, spear-shaped and denticulated appendices 8–12 mm. long and 6–9 mm. broad.

*Size.*—Length 30–35 mm., including the appendices. Breadth at the base 6–9 mm.

*Colour.*—Right side Willow Green (HCC page 199, shade 62/1) with delicately shaded specks of Pomegranate Red (HCC page 192, shade 18/2/3) and covered with fine, wooly tomentum, very short. Underside Spinach Green (HCC page 187, shades 60/1/2/3) more or less tinted over with Pomegranate Red (HCC page 192, shades 18/2/3).

*Surface.*—Outer smooth, glabrous, not very glandular. Inner tomentose, opaque.

*Consistency.*—Average thickness, leathery.

Semi-open flower bud: Globose, roundish, with outer petals only slightly rounded, only slightly separated from the cntral ones, opening gradually in separate whorls with the progress of flowering.

*Size.*—Average length, 30–35 mm.; average diameter, 20–25 mm.

*Colour.*—Between Currant Red (HCC page 167, shades 21–21/1) and Tyre Pink (HCC page 24, shades 24–24/1).

Open Corolla: From medium to large, erect on stem. Regular festooned border with tips only slightly projecting starwise round the border, formed by the meeting of the furling of the outside petals. Hemispherical couple section, with outer petals only slightly drooping on the calyx, rounded on the lateral edges. Corolla flatter in advanced flowering. Inside petals well extended, in layers, curving outwards and only slightly furled on the distal edge. Central petals sometimes a little untidy and arranged dialwise. Centre of flower concave, with stamens and pistils covered by rudimentary petals.

*Size.*—Average diameter with open corolla 80–100 mm. Length of flower 30–40 mm.

*Usual colour.*—Between Blood Red (HCC page 176, shades 20–20/1/2) and Oriental Red (HCC page 175, shades 19–19/1). Petals on an average 50–85 besides 8–10 petaloids at the centre of the flower properly attached to the corolla.

*Shape.*—Outside petals—furled limb with lateral edges converging downwards on sides ¼ or ⅕ of its length, forming one or more sharp points at the points of encounter of the furls. Claws small, only slightly differing. Inside petals—of smaller size, more elongated and with triangular base, narrower and sharper proceeding towards the centre of the flower. Limb often concave at the centre, only slightly furled at the outside towards the tip, without forming points. Claws small, average differentiation.

*Size.*—Outside petals—length, 40–50 mm.; breadth, 40–50 mm. Inside petals—length, 30–45 mm.; breadth, 25–35 mm.

*Colour.*—Right side Oriental Red (HCC page 165, shades 19–19/1/2) with pale velvety shades of Blood Red (HCC page 166, shades 20–20/1) on the outside of the petals and tints of Tyre Pink (HCC page 24, shades 24/2/3) near the claw. Underside—between Currant Red (HCC page 167, shades 21–21/1/2/3) and Cherry Red (HCC page 157, shades 22–22/1) with tints of Tyre Pink (HCC page 24, shades 24/1/2/3) towards the claw. Claw—very small, Primrose Yellow in colour (HCC page 65, shades 1/3) shading off into Tyre Pink at the edge.

*Surface.*—Right side slightly satiny, smooth. Underside idem.

Organs of reproduction: Stamens 70–100 in number, on the outside edge of the thalamus, sometimes in proximity of the stems. Filaments up to 10 mm., tinted with red. Anthers—small, elongated, yellow, binocular.

Styles—average 50–70, in the centre of the thalamus, very slender, twisted, greenish-yellow in colour, in proximity of the base freer at the points. Stigmas—with elongated groove, only slightly differentiated, yellow.

Fruit: Globose, average elongation, with seeds slightly protruding from the thalamus.

Scent: Scarcely perceptible, tea rose perfume.

Resistance of flowers to transport: Excellent.

Resistance of flowers to inclemency of weather: Excellent.

Durability of cut flowers: Excellent.

Resistance of plant to disease: Good.

Flowering: Abundant, even in the winter months.

I claim:

1. Hybrid tea rose plant, with vigorous growth and large dense flowers of a colour between Blood Red and Oriental Red, characterized in that the first plant of this variety was obtained by artificial fecundation of flowers of a hybrid tea rose variety having red flowers with pollen from a hybrid polyantha rose, known as "Ninfa," having red flowers, and said plant having the following unique combination of characteristics:

(a) from the physical standpoint: plant having good height, graceful, vigorous, with compact vegetation and branches only slightly diverging from the axis of the plant; flower stems long and graceful, average occurrence of prickles, large, abundant foliage of a colour which is in harmony with that of the flowers, these being from average to large in size, elegant and regular in shape, many doubles, colour between Blood Red and Oriental Red, borne singly on the flower stems, suitable for commerce and export, (b) from the physiological standpoint: plant highly productive and reflourishing, rapidly growing, not requiring delicate handling in cultivation, suitable for large-scale growing, resistant to disease; flowers withstanding packing, transport and inclemency of weather well, and lasting well when cut.

No references cited.

ROBERT E. BAGWILL, *Primary Examiner.*